United States Patent
Lee et al.

(10) Patent No.: US 12,010,768 B2
(45) Date of Patent: Jun. 11, 2024

(54) HYBRID POWER SUPPLY SYSTEMS, METHODS, AND DEVICES FOR EXCIMER LAMPS

(71) Applicant: GOODRICH CORPORATION, Charlotte, NC (US)

(72) Inventors: Yongduk Lee, Vernon, CT (US); Matthew Robert Pearson, Hartford, CT (US)

(73) Assignee: GOODRICH CORPORATION, Charlotte, NC (US)

( * ) Notice: Subject to any disclaimer, the term of this patent is extended or adjusted under 35 U.S.C. 154(b) by 323 days.

(21) Appl. No.: 17/506,540

(22) Filed: Oct. 20, 2021

(65) Prior Publication Data
US 2023/0119015 A1 Apr. 20, 2023

(51) Int. Cl.
| | |
|---|---|
| H05B 41/28 | (2006.01) |
| A61L 2/10 | (2006.01) |
| A61L 9/20 | (2006.01) |
| H01J 61/56 | (2006.01) |
| H05B 41/04 | (2006.01) |

(52) U.S. Cl.
CPC .......... H05B 41/2806 (2013.01); A61L 2/10 (2013.01); A61L 9/20 (2013.01); H01J 61/56 (2013.01); H05B 41/042 (2013.01); *A61L 2202/11* (2013.01)

(58) Field of Classification Search
CPC .......... H05B 41/2806; H05B 41/042; H05B 41/2828; A61L 9/20; A61L 2/10; A61L 2/24; A61L 2202/11; A61L 2202/14; A61L 2202/25; H01J 61/56; B64F 5/30; B64D 2011/0038; B64D 11/00

USPC .................................... 250/455.11
See application file for complete search history.

(56) References Cited

U.S. PATENT DOCUMENTS

| | | | |
|---|---|---|---|
| 8,344,627 B1 | 1/2013 | Hooke et al. | |
| 8,460,283 B1 | 6/2013 | Laroussi et al. | |
| 11,004,660 B2 | 5/2021 | Prager et al. | |
| 2007/0115088 A1* | 5/2007 | Sugioka | H05B 41/2806 336/232 |
| 2010/0171438 A1 | 7/2010 | Whitt et al. | |
| 2012/0106214 A1 | 5/2012 | Liu et al. | |

FOREIGN PATENT DOCUMENTS

| | | |
|---|---|---|
| CN | 106900135 | 6/2017 |
| CN | 108093551 | 3/2020 |
| CN | 111697869 | 9/2020 |
| KR | 20200091167 | 7/2020 |

OTHER PUBLICATIONS

European Patent Office, European Search Report dated Mar. 15, 2023 in Application No. 22201454.0.
Wang, et al. "Repetitive High-Voltage All-solid-state Marx Generator for Excimer DBD UV Sources", IEEE Transcations on Plasma Science, IEEE Service Center, Piscataway, NJ, US, vol. 44, No. 10, dated Oct. 1, 2016, pp. 1933-1940, XP011625053, ISSN: 0093-3813, DOI: 10.1109/TPS.2016.2558519.

* cited by examiner

Primary Examiner — Kiet T Nguyen
(74) Attorney, Agent, or Firm — SNELL & WILMER L.L.P.

(57) ABSTRACT

A sanitization apparatus includes an excimer lamp, a power converter configured to power the excimer lamp and a controller. The controller is configured to monitor an impedance of the excimer lamp and vary an output voltage waveform of the power converter based upon the impedance.

20 Claims, 7 Drawing Sheets

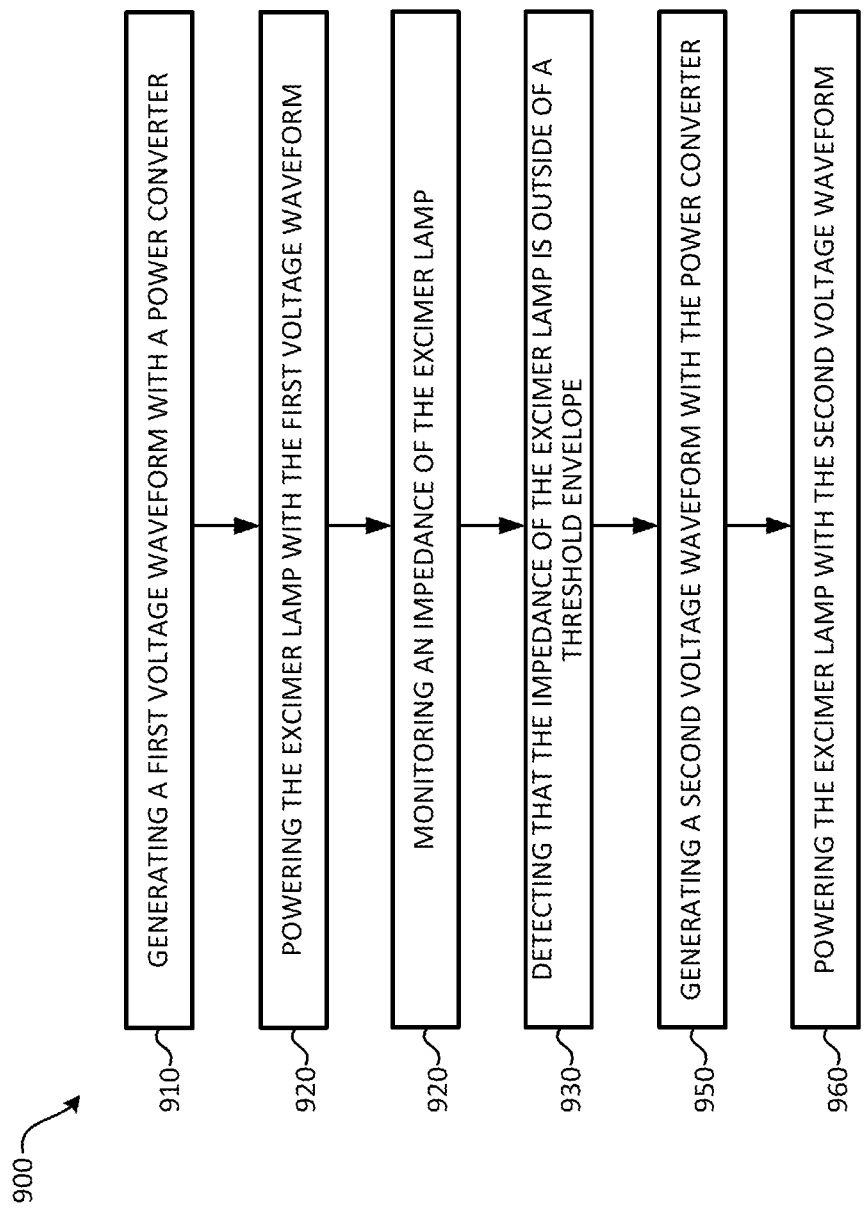

HYBRID POWER SUPPLY SYSTEMS, METHODS, AND DEVICES FOR EXCIMER LAMPS

FIELD

The present disclosure relates generally to sanitization systems and methods and, more particularly, to power supply systems and methods for ultraviolet (UV) light sanitization systems.

BACKGROUND

The recent novel-coronavirus (SARS-COV-2) outbreak has negatively impacted the safety and health of many people. Pathogens can be transmitted via direct airborne transmission between users or via indirect contact transmission from different users occupying the same space at different times. For example, lingering pathogens may remain on contact surfaces of an aircraft cabin to be spread to passengers and/or crew members on a subsequent flight. The safety of passengers and crew members may be improved by performing disinfecting treatments to surfaces, such as seats, ceiling/wall panels, handles, and lavatory surfaces, etc., to mitigate the presence of pathogens on such surfaces. However, conventional disinfection procedures between flights may take time and may thus adversely affect the operating efficiency of the aircraft (increased interval time between flights), and the effectiveness and quality of such conventional treatments are often difficult to verify/track.

SUMMARY

A sanitization apparatus is disclosed, comprising an excimer lamp, a power converter configured to power the excimer lamp, and a controller configured to monitor an impedance of the excimer lamp and vary an output voltage waveform of the power converter based upon the impedance.

In various embodiments, the excimer lamp is configured to emit Far-UVC light.

In various embodiments, the controller is configured to vary the output voltage waveform of the power converter between a sine waveform and a nanosecond pulse voltage.

In various embodiments, the controller is configured to vary the output voltage waveform of the power converter between a first sine waveform comprising a first frequency and a second sine waveform comprising a second frequency, wherein the first frequency is greater than the second frequency.

In various embodiments, the sanitization apparatus further comprises a DC power source configured to supply an input power signal to the power converter.

In various embodiments, the controller is configured to receive a temperature of the excimer lamp, an output current of the power converter, and an output voltage of the power converter.

In various embodiments, the controller is configured to calculate a phase difference between the output current and the output voltage.

In various embodiments, the controller is configured to calculate the impedance based upon the phase difference.

In various embodiments, the controller is configured to calculate the impedance based upon the temperature of the excimer lamp.

A sanitization apparatus is disclosed, comprising an excimer lamp, a power converter configured to power the excimer lamp, and a control unit having a processor, and a tangible, non-transitory memory configured to communicate with the processor. The tangible, non-transitory memory has instructions stored thereon that, in response to execution by the processor, cause the control unit to perform operations comprising generating a first voltage waveform with the power converter, powering the excimer lamp with the first voltage waveform, monitoring an impedance of the excimer lamp, detecting that the impedance of the excimer lamp is outside of a threshold envelope, generating a second voltage waveform with the power converter, and powering the excimer lamp with the second voltage waveform.

In various embodiments, the excimer lamp is configured to emit Far-UVC light.

In various embodiments, the first voltage waveform comprises a sine waveform and the second voltage waveform comprises a nanosecond pulse voltage.

In various embodiments, the first voltage waveform comprises a first frequency and the second first voltage waveform comprises a second frequency, wherein the first frequency is greater than the second frequency.

In various embodiments, the sanitization apparatus further comprises a DC power source configured to supply an input power signal to the power converter.

In various embodiments, the control unit further performs operations comprising receiving a temperature signal of the excimer lamp, receiving an output current signal of the power converter, and receiving an output voltage signal of the power converter, wherein the impedance is monitored using at least one of the temperature signal, the output current signal, and the output voltage signal.

A method for powering an excimer lamp is disclosed, comprising generating a first voltage waveform with a power converter, powering the excimer lamp with the first voltage waveform, monitoring an impedance of the excimer lamp, detecting that the impedance of the excimer lamp is outside of a threshold envelope, generating a second voltage waveform with the power converter, and powering the excimer lamp with the second voltage waveform.

In various embodiments, the method further comprises receiving a temperature signal of the excimer lamp, receiving an output current signal of the power converter, and receiving an output voltage signal of the power converter.

In various embodiments, the impedance is monitored using at least one of the temperature signal, the output current signal, and the output voltage signal.

In various embodiments, the method further comprises measuring a phase difference between the output current signal and the output voltage signal.

In various embodiments, the impedance is monitored based upon at least one of the temperature signal of the excimer lamp and the phase difference of the excimer lamp.

The foregoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by refer

FIG. 9 is a process for powering a sanitization apparatus, in accordance with various embodiments.

DETAILED DESCRIPTION

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

As used herein, the term "wide band gap" is used to refer to a device having a semiconductor material which has a bandgap in the range of 2-4 electronvolt (eV). Examples of wide band gap semiconductor materials include Silicon Carbide (SiC) and Gallium Nitride (GaN).

In various embodiments, Far-UVC (at or near 222 nm wavelength light) has promise to work in occupied spaces. Excimer lamps utilize a high voltage supply and have a large gas discharge. In various embodiments, the systems and methods disclosed herein are configured to determine optimal output voltage waveforms for powering an excimer lamp. In this regard, a sanitization apparatus of the present disclosure may be configured to utilize various output voltage waveforms to optimize electric field distribution of the excimer lamp and improve excimer lamp discharge stability.

In various embodiments, the sanitization systems disclosed herein, utilize an estimation algorithm for maintaining an impedance of an excimer lamp at or near a desired impedance. The sanitization apparatus disclosed herein tends to increase the life of Far-UVC excimer lamps, increase efficiency of startup and ignition of Far-UVC excimer lamps, decrease time to startup of Far-UVC excimer lamps, and provide a more stable gas discharge with respect to changing environmental conditions.

Figure 1:
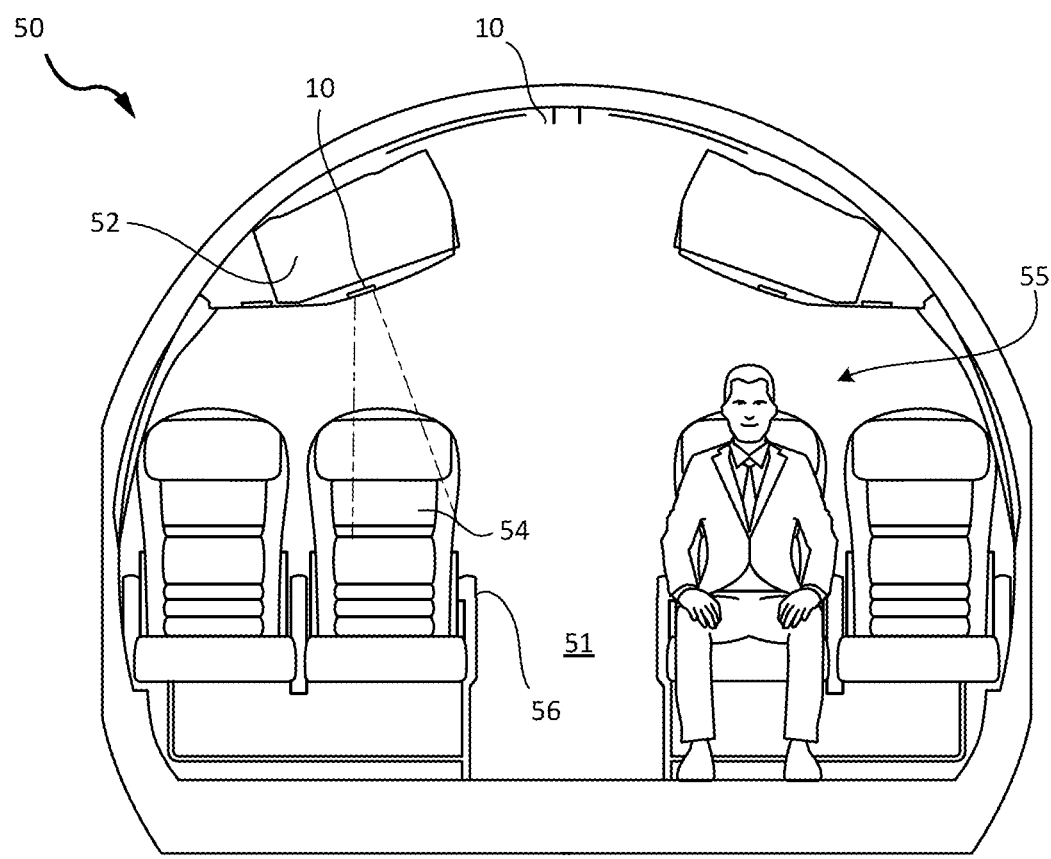
- FIG. 1 illustrates a view of a cabin of an aircraft, in accordance with various embodiments.

With reference to FIG. 1, a cabin 51 of an aircraft 50 is shown, according to various embodiments. The aircraft 50 may be any aircraft such as an airplane, a helicopter, or any other aircraft. The aircraft 50 may include various lighting systems 10 that emit visible light to the cabin 51. Pathogens, such as viruses and bacteria, may remain on surfaces of the cabin 51, and these remaining pathogens may result in indirect contact transmission to other people (e.g., subsequent passengers). For example, the cabin 51 may include overhead bins 52, passenger seats 54 for supporting passengers 55, handles 56, lavatory surfaces, and other structures/surfaces upon which active pathogens may temporarily reside. As will be discussed further below, in order to reduce the transmission/transfer of pathogens between passengers, one or more of the lighting systems 10 may blend disinfecting electromagnetic radiation output into the visible light in order to facilitate disinfection of the cabin 51 (e.g., during flights and/or between flights). The lighting systems 10 may be broken down into different addressable lighting regions that could be used on an aircraft. For example, the regions on an aircraft may include sidewall lighting, cross-bin lighting, over wing exit lighting, ceiling lighting, direct lighting, flex lights, reading lights, dome lights, lavatory lights, mirror lights, cockpit lights, cargo lights, etc. The regional breakdown of the lighting system allows lighting control over broad areas of the aircraft. In various embodiments, lighting system 10 may be disposed in/incorporated by a passenger service unit (PSU) for a row of seats. As such, a lighting system 10 could be provided for each row of an aircraft, as well as for each section of different sections of a given row of an aircraft.

Figure 2:
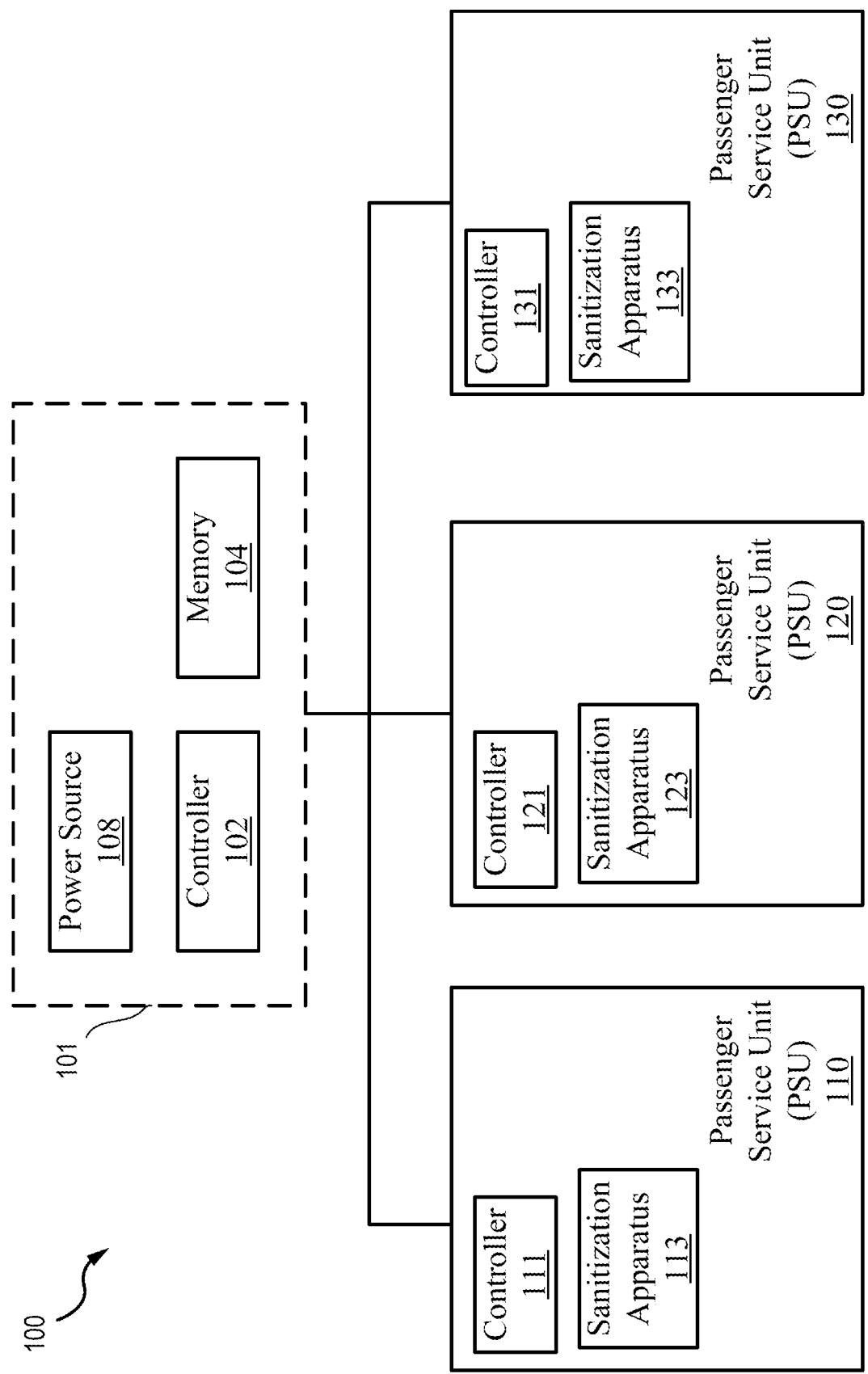
FIG. 2 illustrates a schematic view of a sanitization system, in accordance with various embodiments.

Referring now to FIG. 2 a schematic view of a sanitization system 100 for an aircraft cabin, is illustrated, in accordance with various embodiments. In various embodiments, the sanitization system 100 comprises a main control system 101 and a plurality of PSUs (e.g., first PSU 110, second PSU 120, third PSU 130, etc.). Although illustrated as including three PSUs, the number of PSUs of a sanitization system 100 is not limited in this regard. For example, a PSU may be disposed in each row of seats disposed in a respective column of an aircraft cabin. For example, a cabin with 50 rows and 3 columns may have 150 PSUs (e.g., each row in each column having a PSU). In various embodiments, the PSUs are not limited to rows in the aircraft cabin and may be placed throughout the aircraft cabin as well. For example, PSUs, in accordance with the present disclosure, may be disposed in the lavatory, aisles, cockpit, or any other area of an aircraft cabin where it may be desirable to have sanitization.

In various embodiments, the main control system 101 includes a controller 102 (also referred to herein as a control unit) and a memory 104 (e.g., a database or any appropriate data structure; hereafter "memory 104" also may be referred to as "database 104"). The controller 102 may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controller 102 may utilize one or more processors of any appropriate type/configuration, may utilize any appropriate processing architecture, or both). In various embodiments, the controller 102 may further include any non-transitory memory known in the art. The memory 104 may store instructions usable by the logic device to perform operations. Any appropriate computer-readable type/configuration may be utilized as the memory 104. Any appropriate data storage architecture may be utilized by the memory 104.

The database 104 may be integral to the main control system 101 or may be located remote from the main control system 101. The controller 102 may communicate with the database 104 via any wired or wireless protocol. In that regard, the controller 102 may access data stored in the database 104. In various embodiments, the controller 102 may be integrated into computer systems onboard an aircraft. Furthermore, any number of conventional techniques for electronics configuration, signal processing and/or control, data processing and the like may be employed. Also, the processes, functions, and instructions may include software routines in conjunction with processors, etc.

System program instructions and/or controller instructions may be loaded onto a non-transitory, tangible computer-readable medium having instructions stored thereon that, in response to execution by the processor, cause the controller 102 to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The instructions stored on the memory 104 of the controller 102 may be configured to perform various operations, such as performing cleaning schedules between flights, performing cleaning schedules at predetermined intervals, cleaning a specific row in response to a trigger (i.e., a sneeze or the like), etc.

In various embodiments, the main control system 101 from FIG. 2 further comprises a power source 108. The power source 108 may comprise any power source known in the art, such as a battery, a solar source, an alternating current (AC) source, a direct current (DC) source, a rechargeable source, or the like.

In various embodiments, the main control system 101 is in operable communication with each PSU in the plurality of PSUs (e.g., PSUs 110, 120, 130). In various embodiments, each PSU comprises a local controller (e.g., controllers 111, 121, 131) (also referred to herein as a control unit). Each local controller (e.g., controllers 111, 121, 131) may be in accordance with main controller 102). For example, each local controller (e.g., controllers 111, 121, 131) may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controllers 111, 121, 131 may utilize one or more processors of any appropriate type/configuration, may utilize any appropriate processing architecture, or both). In various embodiments, the controllers 111, 121, 131 may each further include any non-transitory memory that is known in the art. The memory may store instructions usable by the logic device to perform operations. Any appropriate computer-readable type/configuration may be utilized as the memory. Any appropriate data storage architecture may be utilized by the memory.

In various embodiments, each PSU (e.g., PSUs 110, 120, 130) may comprise a sanitization apparatus (e.g., sanitization apparatus 113, 123, 133). As described further herein, the controller 102 may command the various local controllers (e.g., controllers 111, 121, 131) to instruct the devices therein. In various embodiments, the power source 108 is sized and configured to power all of the sanitization apparatus (e.g., sanitization apparatus 113, 123, 133) of all of the PSUs (e.g., PSUs 110, 120, 130, etc.) of sanitization system 100.

In various embodiments, each sanitization apparatus (e.g., sanitization apparatus 113, 123, 133) may be connected via digital communications, discrete communications, or wireless communications to a respective local controller (e.g., controllers 111, 121, 131).

In various embodiments, the sanitization apparatus 113 may comprise a Far-UVC light source. Sanitization apparatus 113 may comprise an excimer lamp. In various embodiments, any light source capable of outputting a light with a wavelength of about 222 nm is within the scope of this disclosure. Sanitization apparatus 113 may be configured to generate a Far-UVC light having a wavelength of between 200 and 230 nm, in accordance with various embodiments. Sanitization apparatus 113 may be configured to generate a Far-UVC light having a wavelength of between 200 and 225 nm, in accordance with various embodiments. Sanitization apparatus 113 may be configured to generate a Far-UVC light having a wavelength of between 207 and 225 nm, in accordance with various embodiments. Sanitization apparatus 113 may be configured to generate a Far-UVC light having a wavelength of about 222 nm, wherein the term "about" in this regard can only refer to a wavelength of 222 nm±15 nm. In various embodiments, the sanitization apparatus 113 is in operable communication with local controller 111 and/or a main controller 102. In this regard, in response to receiving a signal from a controller (e.g., local controller 111 and/or a main controller 102), the light source may be activated and generate Far-UVC disinfecting light.

Figure 3:
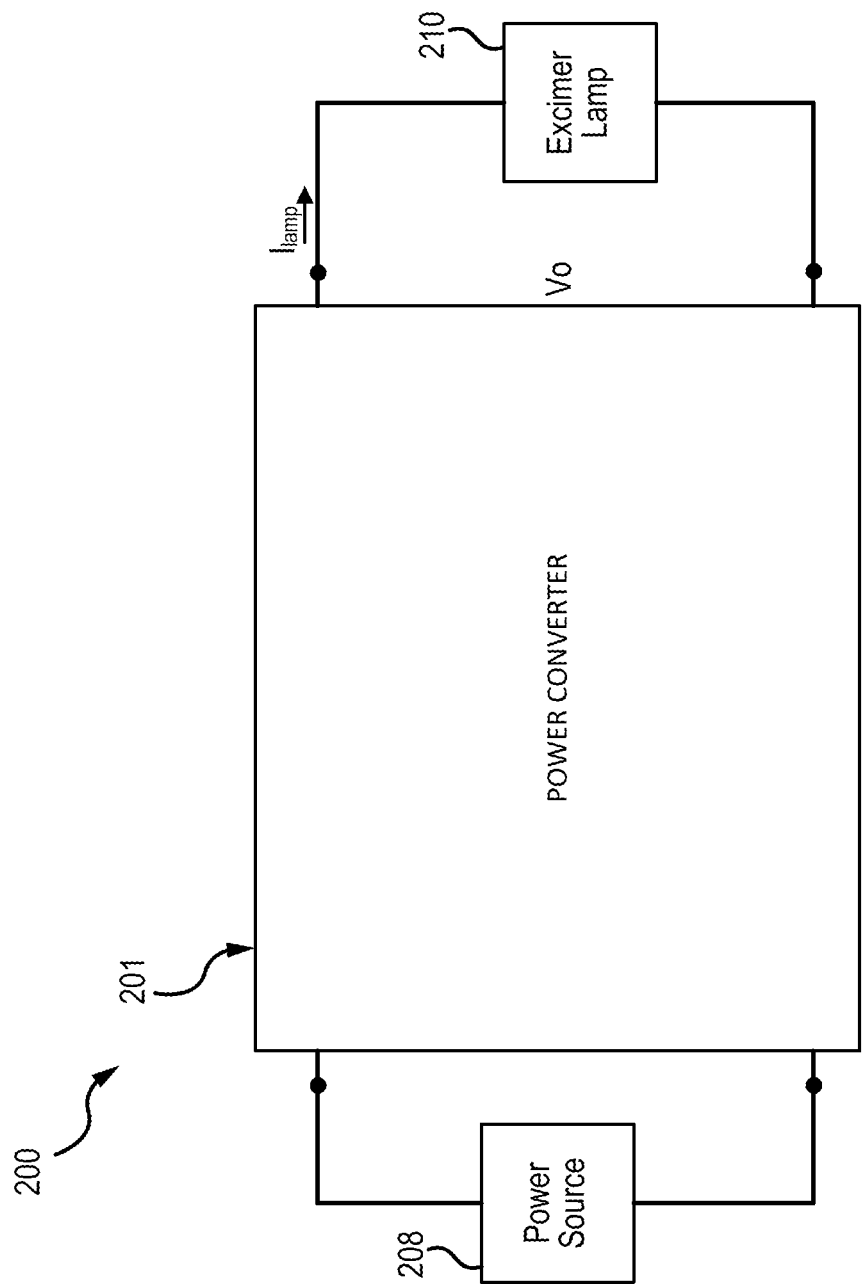
FIG. 3 illustrates a schematic view of a sanitization apparatus connected with a power source, in accordance with various embodiments.

With reference to FIG. 3, a schematic view of a sanitization apparatus 200 connected with a power source 208 is illustrated, in accordance with various embodiments. In various embodiments, sanitization apparatus 200 is similar to sanitization apparatus 113 of FIG. 2. Sanitization apparatus 200 includes an excimer lamp 210. Sanitization apparatus 200 includes a power converter 201 for supplying power to excimer lamp 210. Power converter 201 may receive an input power signal from power source 208. Power converter 201 may receive an input power signal from power source 208 comprising a 28 volt DC power signal, though other voltage levels are contemplated herein, such as 12V DC and 48V DC.

In various embodiments, power converter 201 comprises a wide band gap device, a capacitor, and an inductor. In various embodiments, the wide band gap device comprises a transistor. In various embodiments, power source 208 is configured to charge the capacitor of power converter 201 when the wide band gap device is in an OFF state.

In various embodiments, excimer lamp 210 functions based on a dielectric barrier discharging. The dielectric barrier discharging may have non-linear characteristics. In this regard, the initial ignition and normal steady state may have different load conditions. As the temperature and load environment changes (e.g., altitude), the internal dielectric barrier discharging condition can be changed. Due to these issues, it tends to be difficult to maintain homogenous dielectric barrier discharge for Far-UVC 222 nm.

In order to optimize operation of excimer lamp 210 under various non-linear characteristics and environment changes, the power converter 201 of the present disclosure utilizes a hybrid high frequency sine and nanosecond pulse excitation. A high frequency sine voltage (see FIG. 4) can generate entire bipolar energy injection. This method can remove the remaining energy inside excimer lamp 210. However, at steady state, stable operation, this high frequency sine voltage tends to inject higher energy than desired. In contrast, nanosecond pulse voltage (see FIG. 5 and FIG. 6) tends to be more suitable at steady state, stable operation. However, in response to environmental changes, the nanosecond pulse voltage may not be suitable to generate an appropriate voltage waveform. In this regard, sanitization apparatus 200 may utilize a hybrid output voltage waveform based upon operating conditions.

Figure 4:
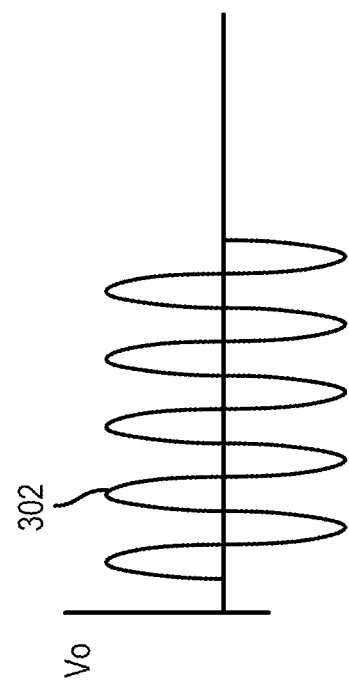
FIG. 4 illustrates a plot of an output voltage signal comprising a high frequency sine wave of the power converter of FIG. 3 during operation of the sanitization apparatus, in accordance with various embodiments.

FIG. 4 illustrates a power supply output voltage waveform 302 for a 222 nm Far-UVC excimer lamp (e.g., excimer lamp 210). Waveform 302 may comprise a high frequency sine wave. As used herein, "high frequency" may refer to a frequency of between 50 and 500 kilohertz (50-500 kHz). Waveform 302 may comprise a peak voltage of between 3 and 6 kilovolts (3-6 kV). With combined reference to FIG. 3 and FIG. 4, power converter 201 may be configured to output voltage waveform 302 for powering excimer lamp 210.

Figure 5:
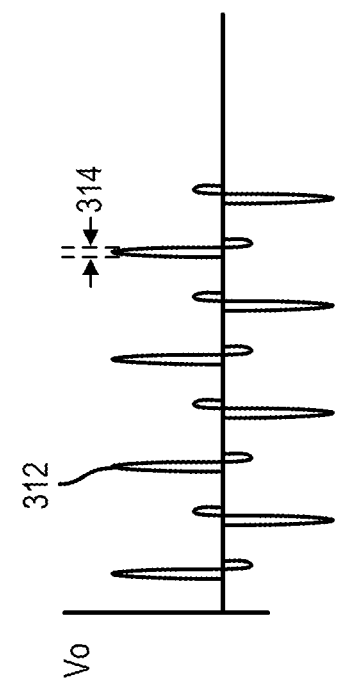
FIG. 5 illustrates a plot of an output voltage signal comprising a bipolar nanosecond pulse waveform of the power converter of FIG. 3 during operation of the sanitization apparatus, in accordance with various embodiments.

FIG. 5 illustrates a power supply output voltage waveform 312 for a 222 nm Far-UVC excimer lamp (e.g., excimer lamp 210). Waveform 312 may comprise a bipolar nanosecond pulse wave. Waveform 312 may comprise a pulse duration 314 of less than 500 nanoseconds. Waveform 312 may comprise a peak voltage of between 3 and 6 kilovolts (3-6 kV). With combined reference to FIG. 3 and FIG. 5, power converter 201 may be configured to output voltage waveform 312 for powering excimer lamp 210.

Figure 6:
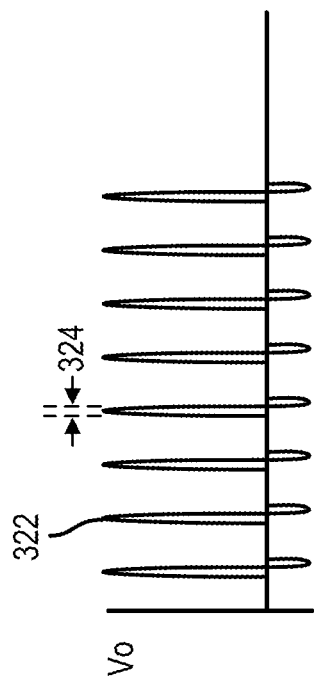
FIG. 6 illustrates a plot of an output voltage signal comprising a unipolar nanosecond pulse waveform of the power converter of FIG. 3 during operation of the sanitization apparatus, in accordance with various embodiments.

FIG. 6 illustrates a power supply output voltage waveform 322 for a 222 nm Far-UVC excimer lamp (e.g., excimer lamp 210). Waveform 322 may comprise a unipolar nanosecond pulse wave. Waveform 322 may comprise a pulse duration 324 of less than 500 nanoseconds. Waveform 322 may comprise a peak voltage of between 3 and 6 kilovolts (3-6 kV). With combined reference to FIG. 3 and FIG. 6, power converter 201 may be configured to output voltage waveform 322 for powering excimer lamp 210.

In various embodiments, the topology of power converter 401 may allow to achieve a desired output voltage shape for excimer lamp 210 without the use of a transformer.

Figure 7:
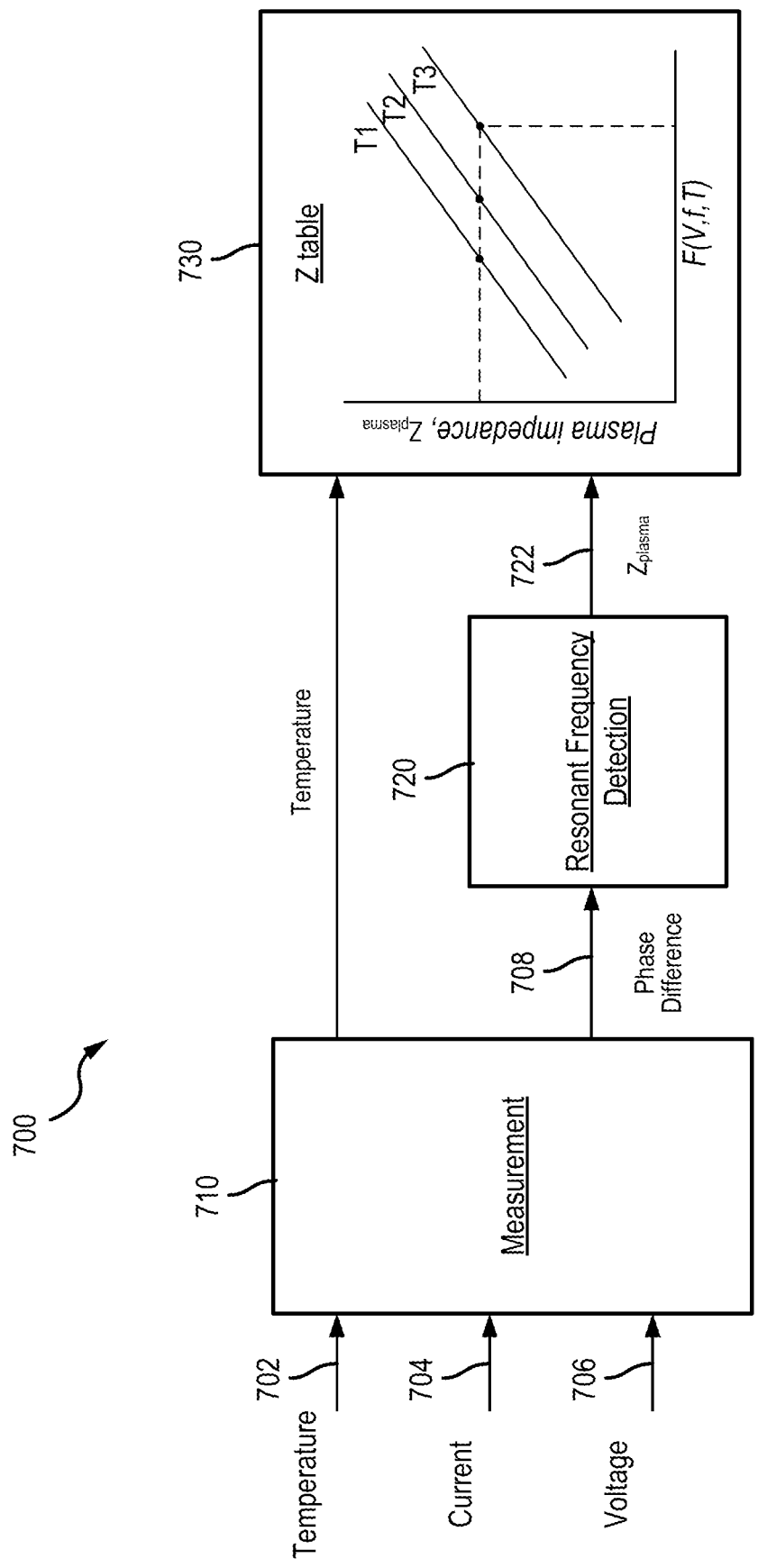
FIG. 7 illustrates an estimation algorithm for controlling electric power supplied to a sanitization apparatus, in accordance with various embodiments.

With reference to FIG. 7, an estimation algorithm 700 is illustrated for determining an optimal output voltage waveform type (e.g., power supply output voltage waveforms 302, 312, 322). In various embodiments, estimation algorithm 700 may be implemented by controller 111 and/or a main controller 102 of FIG. 2 to control the waveform of output voltage Vo (see FIG. 3) of power converter 201 during operation of excimer lamp 210. Estimation algorithm 700 may comprise instructions and/or data stored in memory and configured to be implemented on controller 111 and/or a main controller 102 of FIG. 2. Estimation algorithm 700 may include a measurement logic 710. Measurement logic 710 may receive a temperature 702 measurement, a current 704 measurement, and a voltage 706 measurement. In various embodiments, temperature 702 is an operating temperature of excimer lamp 210 (see FIG. 3). In various embodiments, current 704 is the electrical current $I_{lamp}$ (see FIG. 3) supplied to excimer lamp 210 (see FIG. 3) from power converter 201 (see FIG. 3). In various embodiments, voltage 706 is output voltage Vo (see FIG. 3).

In various embodiments, estimation algorithm 700 may measure a phase difference 708 between current 704 and voltage 706. Estimation algorithm 700 may further include a resonance frequency detection logic 720. Resonance frequency detection logic 720 may receive phase difference 708 and calculate an impedance ($Z_{plasma}$) 722 of excimer lamp 210. Resonance frequency detection logic 720 may calculate impedance 722 of excimer lamp 210 based upon phase difference 708.

As used herein, impedance ($Z_{plasma}$)=R+jXL+jXC, where is R=V/I, XL=$2\pi fL$, and XC=$2\pi fC$.

As used herein, power (P)=VIcosθ, where V is the measured RMS voltage, I is the measured RMS current and θ is the phase difference 708.

Resonance frequency detection logic 720 may calculate impedance ($Z_{plasma}$) as follows: $Z_{plasma}=(V^2/P) \cos \theta = \sqrt{(R^2+(jXL-jXC)^2)}$.

Estimation algorithm 700 may further include an impedance table 730. In various embodiments, impedance table 730 is stored in memory. In various embodiments, impedance table 730 is calculated using temperature 702, current 704, and voltage 706 measurements. In various embodiments, impedance table 730 may comprise empirical data.

Figure 8:
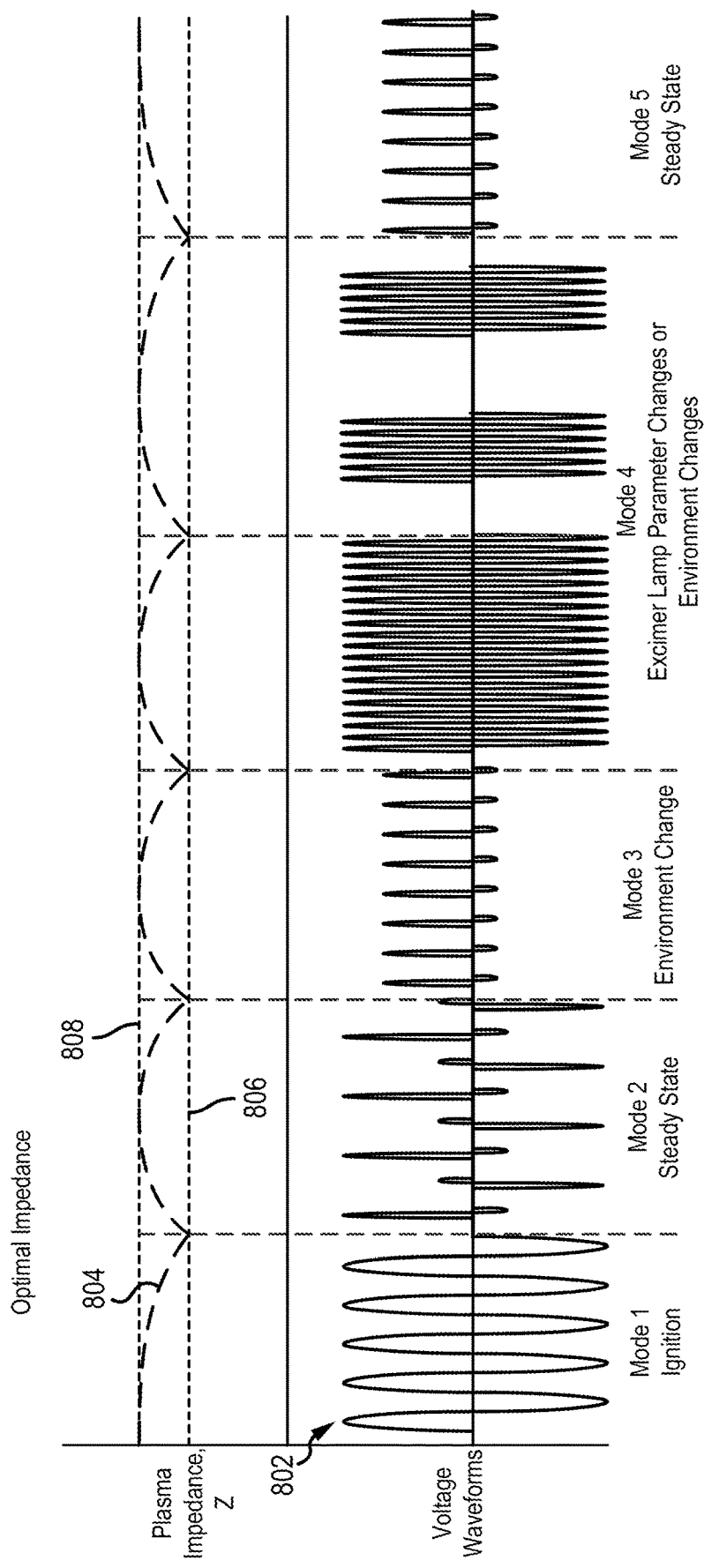
FIG. 8 illustrates various modes of output voltage waveform supplied to a sanitization apparatus and corresponding plasma impedance of the sanitization apparatus, in accordance with various embodiments.

FIG. 8 illustrates a voltage waveform 802 having various modes during operation of an excimer lamp (e.g., excimer lamp 210 of FIG. 3), in accordance with various embodiments. In a first mode, a power converter (e.g., power converter 201 of FIG. 3) may output a first waveform (e.g., see waveform 302 of FIG. 4), such as a sine waveform. In this regard, a controller (e.g., controller 102 and/or controller 111 of FIG. 2) may command the first waveform at the start-up operation (Mode 1) of the excimer lamp. The first waveform may be a high frequency AC resonant voltage. After full excitation of the excimer lamp, the applied voltage may be switched from AC resonant voltage (Mode 1) to a nanosecond pulse voltage (Mode 2) (e.g., see waveform 312 of FIG. 5) to stabilize a normal operation. In response to an environment change (e.g., a change in temperature, altitude, etc.) a unipolar pulse (Mode 3) (e.g., see waveform 322 of FIG. 6) may be applied to minimize the excitation level of the excimer lamp. After some parameter or environment changes (Mode 4), a higher frequency sine waveform can be applied to inject more energy and for impedance matching. After stabilizing the excimer lamp condition, it may be desirable to adjust the energy level of the excimer lamp. In this regard, the resonant frequency of the waveform may remain constant, but a periodic operation may be applied (Mode 4). After stabilizing the load of the excimer lamp, minimum energy injection may be applied (Mode 5) for example using a unipolar pulse.

The output voltage waveform 802 may be adjusted based upon the measured impedance ($Z_{plasma}$) 804 (e.g., see impedance 722 of FIG. 7) of the excimer lamp. The output voltage waveform 802 may be adjusted between various modes to maintain impedance 804 within a predetermined envelope. For example, a controller may adjust output voltage waveform 802 to maintain impedance 804 between a minimum impedance threshold value 806 and a maximum impedance threshold value 808.

With reference to FIG. 9, a method 900 is illustrated, in accordance with various embodiments. Method 900 may be for powering a 222 nm Far-UVC excimer lamp. Method 900 includes generating a first voltage waveform with a power converter (step 910). Method 900 includes powering the excimer lamp with the first voltage waveform (step 920). Method 900 includes monitoring an impedance of the excimer lamp (step 930). Method 900 includes detecting that the impedance of the excimer lamp is outside of a threshold envelope (step 940). Method 900 includes generating a second voltage waveform with the power converter (step 950). Method 900 includes powering the excimer lamp with the second voltage waveform (step 960).

With combined reference to FIG. 3 and FIG. 9, step 910 may include generating, by power converter 201, a first voltage waveform (e.g., waveform 302, waveform 312, or waveform 322). Step 920 may include powering the excimer lamp 210 with the first voltage waveform. Step 930 may include monitoring (e.g., by controller 102 and/or controller 111 of FIG. 2 using estimation algorithm 700 of FIG. 7) an impedance $Z_{plasma}$ of the excimer lamp 210. Step 940 may include detecting (e.g., by controller 102 and/or controller 111 of FIG. 2) that the impedance $Z_{plasma}$ of the excimer lamp 210 is outside of a threshold envelope (e.g., above threshold value 808 or below threshold value 806 of FIG. 8). Step 950 may include generating, by power converter 201, a second voltage waveform (e.g., another of the waveform 302, waveform 312, or waveform 322). Step 960 may include powering the excimer lamp 210 with the second voltage waveform.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A sanitization apparatus comprising:
an excimer lamp;
a power converter configured to power the excimer lamp; and
a controller configured to monitor an impedance of the excimer lamp and vary an output voltage waveform of the power converter based upon the impedance.

2. The sanitization apparatus of claim 1, wherein the excimer lamp is configured to emit Far-UVC light.

3. The sanitization apparatus of claim 2, wherein the controller is configured to vary the output voltage waveform of the power converter between a sine waveform and a nanosecond pulse voltage.

4. The sanitization apparatus of claim 2, wherein the controller is configured to vary the output voltage waveform of the power converter between a first sine waveform comprising a first frequency and a second sine waveform comprising a second frequency, wherein the first frequency is greater than the second frequency.

5. The sanitization apparatus of claim 2, further comprising a DC power source configured to supply an input power signal to the power converter.

6. The sanitization apparatus of claim 1, wherein the controller is configured to receive a temperature of the excimer lamp, an output current of the power converter, and an output voltage of the power converter.

7. The sanitization apparatus of claim 6, wherein the controller is configured to calculate a phase difference between the output current and the output voltage.

8. The sanitization apparatus of claim 7, wherein the controller is configured to calculate the impedance based upon the phase difference.

9. The sanitization apparatus of claim 8, wherein the controller is configured to calculate the impedance based upon the temperature of the excimer lamp.

10. A sanitization apparatus comprising:
an excimer lamp;
a power converter configured to power the excimer lamp; and
a control unit having a processor; and
a tangible, non-transitory memory configured to communicate with the processor, the tangible, non-transitory memory having instructions stored thereon that, in response to execution by the processor, cause the control unit to perform operations comprising:
generating a first voltage waveform with the power converter;
powering the excimer lamp with the first voltage waveform;
monitoring an impedance of the excimer lamp;
detecting that the impedance of the excimer lamp is outside of a threshold envelope;
generating a second voltage waveform with the power converter; and
powering the excimer lamp with the second voltage waveform.

11. The sanitization apparatus of claim 10, wherein the excimer lamp is configured to emit Far-UVC light.

12. The sanitization apparatus of claim 10, wherein the first voltage waveform comprises a sine waveform and the second voltage waveform comprises a nanosecond pulse voltage.

13. The sanitization apparatus of claim 10, wherein the first voltage waveform comprises a first frequency and the second voltage waveform comprises a second frequency, wherein the first frequency is greater than the second frequency.

14. The sanitization apparatus of claim 10, further comprising a DC power source configured to supply an input power signal to the power converter.

15. The sanitization apparatus of claim 10, wherein the control unit further performs operations comprising:
receiving a temperature signal of the excimer lamp;
receiving an output current signal of the power converter; and
receiving an output voltage signal of the power converter;
wherein the impedance is monitored using at least one of the temperature signal, the output current signal, and the output voltage signal.

16. A method for powering an excimer lamp, comprising:
generating a first voltage waveform with a power converter;
powering the excimer lamp with the first voltage waveform;
monitoring an impedance of the excimer lamp;
detecting that the impedance of the excimer lamp is outside of a threshold envelope;
generating a second voltage waveform with the power converter; and
powering the excimer lamp with the second voltage waveform.

17. The method of claim 16, further comprising:
receiving a temperature signal of the excimer lamp;
receiving an output current signal of the power converter; and
receiving an output voltage signal of the power converter.

18. The method of claim 17, wherein the impedance is monitored using at least one of the temperature signal, the output current signal, and the output voltage signal.

19. The method of claim 18, further comprising measuring a phase difference between the output current signal and the output voltage signal.

20. The method of claim 19, wherein the impedance is monitored based upon at least one of the temperature signal of the excimer lamp and the phase difference of the excimer lamp.

* * * * *